United States Patent [19]

Okada

[11] Patent Number: 4,558,691

[45] Date of Patent: Dec. 17, 1985

[54] ENDOSCOPE

[75] Inventor: Minoru Okada, Hachioji, Japan

[73] Assignee: Olympus Optical Co. Ltd., Japan

[21] Appl. No.: 628,254

[22] Filed: Jul. 6, 1984

[30] Foreign Application Priority Data

Aug. 18, 1983 [JP] Japan ................. 58-150501

[51] Int. Cl.$^4$ ............................................. A61B 1/06
[52] U.S. Cl. ........................................ 128/6; 350/96.26
[58] Field of Search ................. 128/4, 6; 350/96.26; 354/372, 379, 383, 384

[56] References Cited

U.S. PATENT DOCUMENTS

| 3,730,632 | 5/1973 | Chikama | 128/6 X |
| 3,817,619 | 6/1974 | Kawahara | 128/6 X |
| 3,817,631 | 6/1974 | Kawahara | 128/6 X |
| 3,817,635 | 6/1974 | Kawahara | 128/6 X |
| 3,819,267 | 6/1974 | Kawahara | 128/6 X |
| 4,271,829 | 6/1981 | Heckele | 128/6 |

FOREIGN PATENT DOCUMENTS 49-44752  11/1974  Japan .

*Primary Examiner*—William H. Grieb
*Attorney, Agent, or Firm*—Ostrolenk, Faber, Gerb & Soffen

[57] ABSTRACT

An endoscope includes an indicating index disposed between an objective optical system and an image transmitter so as to be movable in cooperation with the objective optical system through a cam mechanism and a stationary reference index disposed in a path for transmitting an image of an object to be observed, so that measurements of an actual size of the object, a magnification of the objective optical system, an object distance and the like can be made in a reliable manner based on the positional relationship between the indicating index and the stationary reference index, although the objective optical system moves due to a focus adjustment operation. In addition, an endoscope is provided with a plurality of the stationary reference indexes so that the above mentioned measurements can be made in a reliable manner, although the objective optical system moves by operation of an angle of view converting apparatus.

16 Claims, 21 Drawing Figures

ENDOSCOPE

BACKGROUND OF THE INVENTION

The present invention relates to an endoscope, and more particularly, to an endoscope which is capable of indicating an actual size of an object being observed, a magnification of an objective optical system, a distance to the object being observed and the like in a visual field.

By way of example, an endoscope having an actual size indicator is disclosed in Japanese Patent Publication No. Sho 49/1974-44752. This endoscope has been known as the one which is capable of measuring an actual size of an affected part within a coeliac cavity or of an object being observed such as a foreign substance.

The endoscope just described produces an electrical signal corresponding to a relative movement between an objective lens barrel which is movable along its optical axis to make a focus adjustment and an image transmitter which faces one end of the objective lens barrel and cooperatively moves a measure indicator disposed at a light exit end portion which is the other end of the image transmitter in response to the electrical signal to allow an indication of a length in the measure indicator to vary in proportion to the relative movement.

However, the endoscope includes a potentiometer at its distal end portion which potentiometer comprises a resistor and a slider which moves in cooperation with and in proportion to movement of the objective lens barrel and a d.c. instrument having a rotor in an eyepiece portion of the endoscope. In addition, the endoscope has a wiring in its insertion portion which wiring electrically connects the potentiometer to the d.c. instrument. Consequently, devices specific to the endoscope have to be built in each portion thereof with the result of complication in structure.

U.S. Pat. No. 3,730,632 discloses an endoscope having a shading plate which is ganged with an objective lens barrel and transmitting a position of the shading plate through a light conductor to a measure indicator as a light signal to allow a length of a bright or a shaded area in the measure indicator to vary so that an actual size of an object being observed can be measured based on the variation of the length.

However, the foregoing endoscope only utilizes an optical means in place of the electrical means in the endoscope of the above-mentioned Japanese patent. As a result a light conducting member has to be further through a distal end portion, an insertion portion and a proximal operation portion of the endoscope in addition to an image transmitter which transmits an image of an object being observed, resulting in complication in structure. In addition, the measure indicator is disposed adjacent to an image exit end plane of the image transmitter and hence it is impossible to make the measurement by superposing an index on an image of an object being observed so that accuracy in the measurement may be limited.

SUMMARY OF THE INVENTION

It is an object of the present invention to provide an endoscope which has an indicating index which is disposed between an objective optical system and an image transmitter so as to cooperate with the objective optical system through a cam mechanism and has a stationary reference index which is disposed in a path for transmitting an image of an object being observed, so that an actual size of the object being observed, a magnification of the objective optical system and the like can be reliably read from the positional relationship between the indicating index and the stationary reference index although the objective optical system moves due to a focus adjustment operation.

It is another object of the present invention to provide an endoscope which has an indicating index which is disposed between an objective optical system and an image transmitter so as to cooperate with the objective optical system through a cam mechanism and a plurality of stationary reference indexes which are disposed in a path for transmitting an image of an object being observed, so that an actual size of the object being observed, a magnification of the objective optical system and the like can be reliably read from a positional relationship between the indicating index and the stationary reference index although the objective optical system moves due to a focus adjustment operation as well as an angle of view of the objective optical system varies with an angle of view converting apparatus.

According to the present invention, the movement of the objective optical system is transmitted as a positional change of the indicating index through the image transmitter to an eyepiece optical system together with an image of an object being observed and hence there is no necessity for arranging a wiring for signals and a light conducting member through the distal end portion, insertion portion and proximal operating portion as in conventional endoscopes. Furthermore, a potentiometer, a d.c. instrument and the like need not to be built in the distal end portion and the proximal operating portion so that the measurement of an actual size of an object being observed and indication of a magnification of the objective optical system can be made with an extremely simple construction.

According to the present invention, a plurality of stationary reference indexes are disposed each of which corresponds to switching of an angle of view by means of an angle of view converting apparatus and hence even when an angle of view of the objective optical system is changed due to a focus adjustment operation as well as switching of an angle of view by means of the angle of view converting apparatus, the measurement of an actual size of an object being observed and indication of a magnification of the objective optical system can be made in a reliable manner.

According to the present invention, since the indicating index and the stationary reference index are displayed in a visual field, the measurement of an actual size of an object being observed can be conducted accurately by superposing both indexes on an image of an object being observed.

DESCRIPTION OF THE PREFERRED EMBODIMENTS

Figure 1:
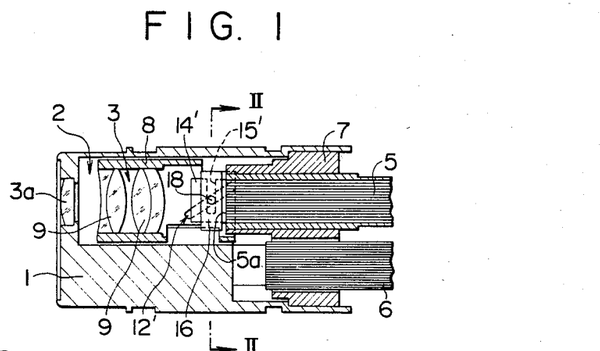
FIG. 1 is a sectional view of a distal end portion of an endoscope according to a first embodiment of the present invention.
Figure 2:
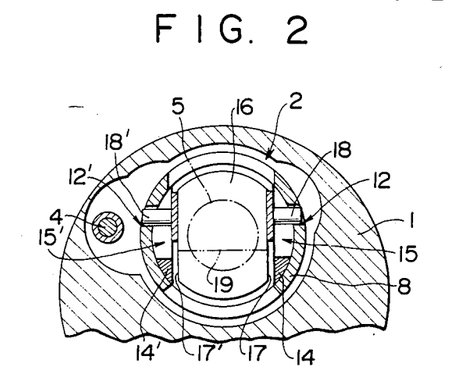
FIG. 2 is a sectional view of essential parts taken along line II—II of FIG. 1.

Referring now to FIG. 1, an endoscope according to one embodiment of the present invention has a housing space 2 for an objective optical system in its distal end portion 1. An objective optical system 3 is housed within the housing space 2 so as to be slidable along its optical axis. The objective optical system 3 is connected through an operating wire 4 (FIG. 2) to an operating member for adjusting a focus (not shown) which is provided in a proximal operating portion of the endoscope and a focus adjustment operation to an object being observed is made by moving the objective optical system 3 back and forth along the optical axis in cooperation with movement of the wire 4. An observation window 3a formed of a cover glass is provided at the front end of the distal end portion 1 which end faces the objective optical system 3.

The rear end of the distal end portion 1 is connected to respective front ends of an image transmitter 5 made of an optical fiber bundle and serving as an image transmitting system and a light transmitter 6 for transmitting an illuminating light. The front end of the image transmitter 5 is secured through a member 7 for receiving the image transmitter to the distal end portion 1. An image receiving end plane 5a of the image transmitter 5 faces the objective optical system 3.

Figure 3:
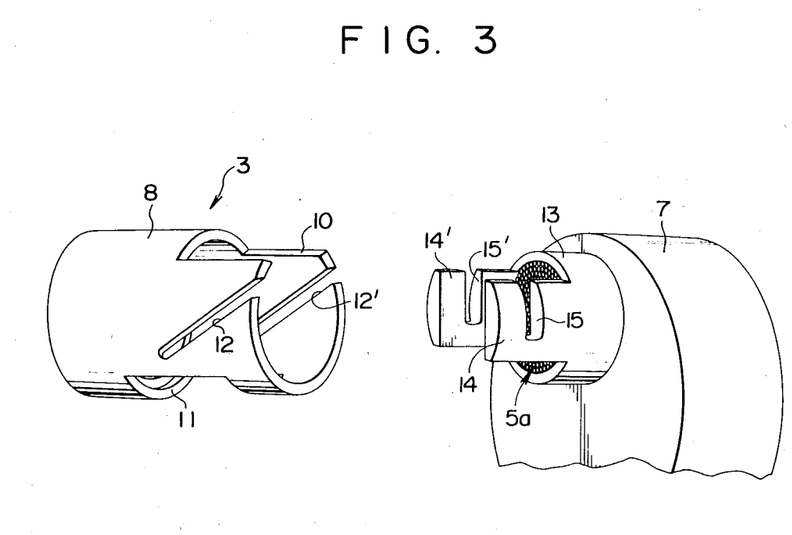
FIG. 3 is a perspective view separately illustrating the lens barrel and a receiving member for an image transmitter shown in FIG. 1.

The objective optical system 3 comprises a cylinder-shaped lens barrel 8 and a plurality of objective lenses 9 which are fitted with the lens barrel 8. At the rear end of the lens barrel 8 are provided a cut portion 10 which is formed by partially and horizontally cutting the upper wall of the lens barrel 8 and an opening 11 on the lower wall of the lens barrel 8, as shown in FIG. 3. In addition, on rear right and left side walls of the lens barrel 8 are provided cam grooves 12, 12' which gradually descend in the forward direction, that is, toward the objective lens 9. The cam grooves 12, 17' are shaped so as to correspond to the relationship between a positional relation between the objective lens 9 and the image transmitter 5 and a magnification of the objective lens 9 for an object being observed under the positional relation.

The receiving member 7 for the image transmitter is projectedly provided with a cylinder portion 13 (FIG. 3) on its front wall such that the cylinder portion 13 encircles the front end part of the image transmitter 5. At the front end of the cylinder portion 13 are further provided a pair of right and left projections 14, 14' which project forwardly of the image receiving end plane 5a. These projections 14, 14' are inserted into the rear end of the lens barrel 8 and are provided with vertically extending control grooves 15, 15' at respective positions facing the cam grooves 12, 12' of the lens barrel 8 with the projections 14, 14' inserted into the rear end of the lens barrel 8. Accordingly, the cam grooves 12, 12' and the control grooves 15, 15' are arranged in an intersecting condition.

A transparent glass plate 16 (FIGS. 1 and 2) for an indication index is disposed perpendicularly to the optical axis of the objective lens between the rearmost objective lens 9 and the image receiving end plane 5a. The glass plate 16 is in a shape in which opposite side portions of a circular disc are cut down in such a manner that their opposite side planes 17, 17' are parallel to one another. Follower pins 18, 18' are projectedly secured to the side planes 17, 17' at positions facing each other. The follower pins 18, 18' fit in the intersections between the cam grooves 12, 12' and the control grooves 15, 15' and go up and down along the cam grooves 12, 12' while being controlled by the control grooves 15, 15' as the lens barrel 8 moves back and forth along the optical axis. Consequently, the glass plate 16 moves only vertically in the plane perpendicular to the optical axis as the lens barrel 8 moves back and forth along the optical axis. On the rear surface of the glass plate 16 is formed an indicating index 19 which is a horizontal line formed by means of an evaporation operation or the like.

Figure 4:
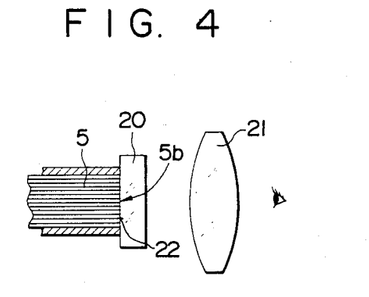
FIG. 4 is a sectional view of essential parts of an eyepiece portion of the endoscope shown in FIG. 1.

The rear end of the image transmitter 5 extends to an eyepiece portion which is disposed in the proximal operating portion of the endoscope and an image exit end plane 5b (FIG. 4) of the image transmitter 5 faces an eyepiece 21 through a transparent glass plate 20 containing a stationary reference index. On the inner plane of the glass plate 20, that is, on the plane of the glass plate which is located on the image exit end plane 5b side, is formed a stationary reference index 22 (FIGS. 5A and 5B) which is a horizontal line by means of an evaporation operation or the like. The inner plane of the glass plate 20 is secured to the image exit end plane 5b.

Figure 5A:
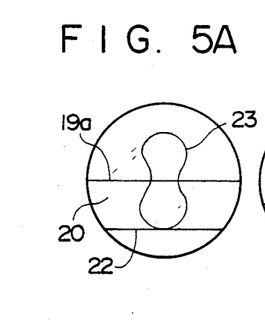
FIGS. 5A and B are views of respective examples of visual fields viewed from the eyepiece portion.
Figure 5B:
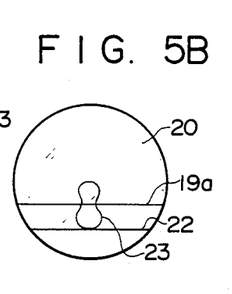

The indicating index 19 and the stationary reference index 22 are both arranged in the path for transmitting an image 23 of an object being observed. An image 19a of the indicating index 19 and the stationary reference index 22 can be simultaneously observed through the eyepiece 21 together with the image 23 (FIGS. 5A and B).

The positional relationship between the image 19a of the indicating index 19 and the stationary reference index 22 can be set by defining the position of the stationary reference index 22 as follows. After an object having a reference length is placed at a predetermined distance from the objective lens 9 and a focus adjustment operation is then made by moving the objective optical system 3 back and forth, the position of the stationary reference index 22 is defined such that the distance between the image 19a and the reference index 22 coincides with the length of the image 23 of the object having a reference length viewing through the eyepiece 21.

In operation, when a focus adjustment operation is made at the proximal operating portion of the endoscope, the operation force is transmitted through the operating wire 4 to the objective optical system 3 to move the latter back and forth along the optical axis. Accordingly, while the focus adjustment operation is conducted viewing through the eyepiece 21, it is possible to bring an image of an object to be observed which is located at a distance into focus on the image receiving end plane 5a through the objective optical system 3.

The follower pins 18, 18' move up and down with movement of the cam grooves 12, 12' under control of the control grooves 15, 15' in cooperation with the movement of the objective optical system 3 during the focus adjustment operation. As a result, the glass plate 16 moves up and down and hence the indicating index 19 which is formed on the glass plate 16 also rises and falls. As the cam grooves 12, 12' are formed to descend forwardly, the glass plate 16 moves up as the lens barrel 8 moves forward and moves down as the lens barrel 8 moves backward. Since the shapes of the cam grooves 12, 12' are defined so as to correspond to the relationship between a relative position of the objective lens 9 to the image transmitter 5 and a magnification of the objective lens 9 for an object being observed at the relative position of the objective lens 9, even when the focus adjustment operation is conducted, the distance between the image 19a and the reference index 22 is always of a given reference length (for example, 1 mm) in real space, as shown in FIGS. 5A and B. Since the image 19a and the reference index 22 can be simultaneously observed through the eyepiece 21, the distance between the image 19a and the reference index 22, that is, the reference length, can be observed together with the object image 23 and an actual size of the object can be measured based on the reference length.

Figure 6:
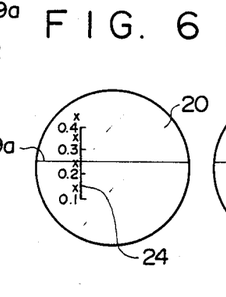
FIGS. 6 and 7 are explanatory views of visual fields illustrating respective modifications of a stationary reference index.
Figure 7:
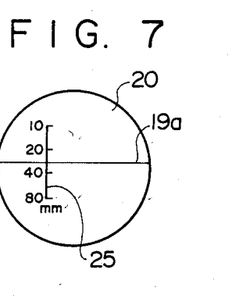

While in the endoscope of the above mentioned embodiment, an actual size of an object to be observed can be measured based on the distance between the stationary reference index 22 which is formed as a horizontal line and the image 19a of the indicating index 19, a stationary reference index 24, as shown in FIG. 6, may be formed by a scale indicating a magnification of the objective optical system 3 or a stationary reference index 25, as shown in FIG. 7, may be formed by a scale indicating a distance between the objective optical system 3 and an object to be observed.

With the stationary reference index 24 or 25, the image 19a of the indicating index 19 moves up and down as the focus adjustment operation is conducted and a magnification of the objective optical system 3 or a distance between the objective optical system 3 and an object being observed can be read by a scale at an intersection between the image 19a and the stationary reference index 24 or 25, respectively.

Figure 8:
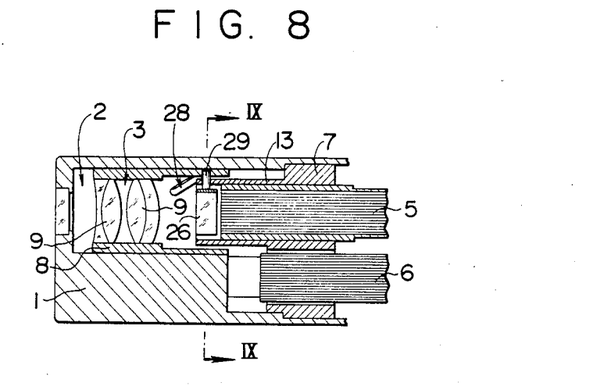
FIG. 8 is a sectional view of a distal end portion of an endoscope according to a second embodiment of the present invention.
Figure 9:
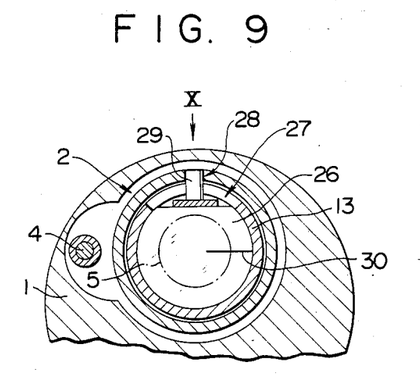
FIG. 9 is a sectional view of essential parts taken along line IX—IX of FIG. 8.
Figure 10:
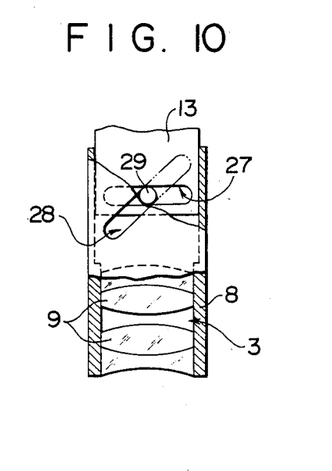
FIG. 10 is a cutaway plan view of essential parts of the distal end portion viewed from the direction indicated by arrow X in FIG. 9.

FIG. 8 illustrates a distal end portion 1 in an endoscope according to another embodiment of the present invention. In the distal end portion 1, a transparent glass plate 26 for an indicating index is disposed so as to be rotatable in the plane perpendicular to the optical axis of the objective optical system 3 as the objective optical system 3 moves back and forth along the optical axis. Specifically, the glass plate 26, as shown in FIG. 9, is in a form in which the upper end portion of a circular disc is cut down and a follower pin 29 is projectedly secured to the upper end plane of the glass plate 26. The follower pin 29 fits in the intersection between a control groove 27 which extends circumferentially on the upper surface wall of the cylinder portion 13 of the image transmitter receiving member 7 and which intersects at right angles with the optical axis and a cam groove 28 which is provided on the upper surface wall portion of the lens barrel 8 which portion is located to face the control groove 27 in such a manner that the cam groove 28 is inclined with respect to both of the optical axis and the circumferential direction of the lens barrel 8 (see FIG. 10). In addition, an indicating index 30 which is a radial line on the glass plate 26 is formed on the rear plane of the glass plate 26 by means of an evaporation operation or the like.

Figure 11:
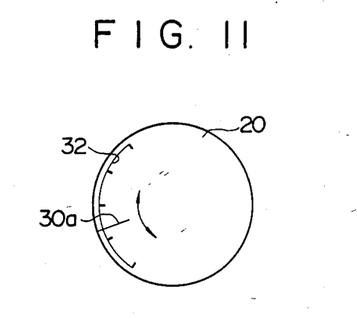
FIG. 11 is an explanatory view of a visual field illustrating an indicating index and a stationary reference index which is viewed from an eyepiece portion of the endoscope shown in FIG. 8.

A stationary reference index is formed on a transparent glass plate which is disposed at the image exit end plane 5b side of the image transmitter 5, as shown in FIG. 11. The stationary reference index 32 has a scale indicating a magnification of the objective optical system 3. The index 32 is formed along the periphery of the glass plate 20, by means of an evaporation operation or the like.

The cam groove 28 is shaped so as to correspond to the relationship between a positional relation between the objective lens 9 and the image transmitter 5 and a magnification of the objective lens 9 for an object being observed under the positional relation of the objective lens 9 to the image transmitter 5.

Those members of the endoscope of the embodiment of FIGS. 8–11 which have not specifically been referred to are constructed in a manner similar to the embodiment of FIG. 1 through FIGS. 5A and B, and like reference characters have been added to FIGS. 8–11 to designate like members of the endoscope. A detailed description of these elements will be omitted (this is also true with respect to the following embodiments).

In operation, when a focus adjustment operation is conducted by moving the objective optical system 3 back and forth, the cam groove 28 of the lens barrel 8 moves so that the intersection between the cam groove 28 and the control groove 27 moves in the circumferential direction. Consequently, the follower pin 29 which fits in the intersection moves in the circumferential direction and the glass plate 26 rotates around the optical axis. As a result, the indicating index 30 also turns integrally. The image 30a (FIG. 11) of the indicating index 30 can be observed through the eyepiece portion of the endoscope together with the stationary reference index 32. The magnification of the objective optical system 3 in the in-focus condition can be given by reading scale indicated by the intersection between the stationary reference index 32 and the image 30a.

A primary advantage of the endoscope of the embodiment just described, wherein the glass plate 26, rotates about the optical axis, is that the distal end portion 1 of the endoscope can be reduced in size compared with that of the embodiment shown in FIGS. 1 to 5A and B in which the glass plate 16 moves up and down.

When using an endoscope, there are times when an angle of view converting apparatus, such as an optical adapter is used in order to change range of the visual field being observed. In such cases, the relationship between the position of the objective lens to the image transmitter and the magnification of the objective lens may vary in accordance with the selected angle of view. In the endoscope of the embodiments described thus far, however, the relationship between the position of the objective lens to the image transmitter and the position of the indicating index in the visual field is defined in accordance with a shape of the cam groove, and is therefore fixed. Accordingly, when a magnification of an image of an object to be observed in the visual field varies by conversion of an angle of view, the actual size of an object to be observed, the magnification of an objective optical system, the distance to the object and the like can not be measured.

Figure 12:
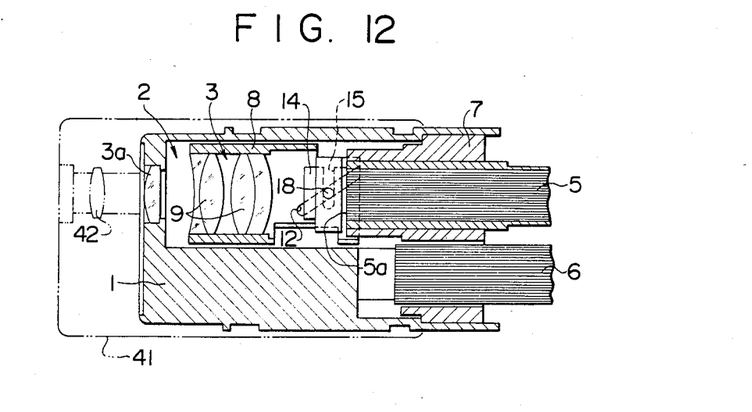
FIG. 12 is a sectional view of a distal end portion of an endoscope according to a third embodiment of the present invention.

FIG. 12 illustrates a further embodiment of the present invention which overcomes this problem. An endoscope according to this embodiment of the invention uses an optical adapter 41 as an angle of view converting apparatus which is removably mounted on the distal end portion 1 thereof. The optical adapter 41 is formed in a cylinder body which faces the observing window 3a of the distal end portion 1 and which includes an angle of view converting lens 42 which is optically coupled to the objective optical system 3. The optical adapter 41 is mounted on the endoscope in such a manner that its rear cylinder portion covers the outer periphery of the distal end portion 1. When the optical adapter 41 is mounted on the endoscope, as shown in FIG. 16, the angle of view is a wide angle $\theta_1$ and when removed the angle of view is a narrow angle $\theta_2$.

Figure 13:
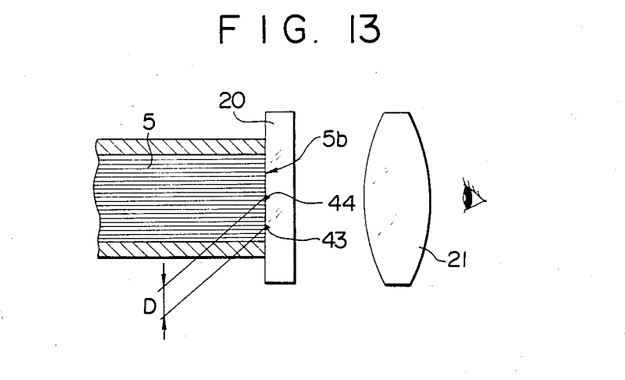
FIG. 13 is a sectional view of essential parts of an eyepiece portion of the endoscope shown in FIG. 12.

In FIG. 13, the stationary reference index is formed on the inner surface of a transparent glass plate 20 which is disposed at the image exit end plate 5b side of the image transmitter 5. The index is defined by first and second stationary reference indexes 43, 44 which are two horizontal parallel lines formed by means of an evaporation operation or the like. The positional relationship between the first stationary reference index 43 and the image 19a of the indicating index 19 is set by defining the position of the reference index 43 as follows. With the optical adapter 41 removed from the endoscope, an object having a known reference length is placed at a distance from the objective lens 9 and a focus adjustment operation is made by moving the objective optical system 3 back and forth. Subsequently, the first reference index 43 is fixed in such a manner that the distance a between the image 19a and the first reference index 43 coincides with the length of the image 23 of the object having the reference length viewed through the eyepiece 21 (see FIGS. 14A and 14B). The positional relationship between the second reference index 44 and the image 19a is set by defining the position of the reference index 44 as follows. With the optical adapter 41 mounted on the endoscope, an object having a known reference length is placed at a distance from the objective lens 9 and a focus adjustment operation is made by moving the objective optical system 3 back and forth. Subsequently, the second reference index 44 is fixed in such a manner that a distance b (FIGS. 15A and 15B) between the image 19a and the second reference index 44 coincides with a length of a given portion of the image 23 of the object having the reference length viewed through the eyepiece lens 21.

Figure 16:
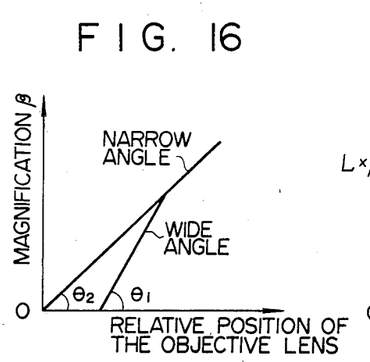
FIG. 16 is a diagram illustrating a relationship between a relative position and a magnification of the objective lens in the endoscope shown in FIG. 12.

The shape of the cam groove 12, as shown in FIG. 16, can be approximated by a straight line and is defined by the relationship between the relative position of the objective lens 9 to the image transmitter 5 and the magnification $\beta$ of the latter. Accordingly, when the reference lengths for a wide and a narrow angles of view are represented by the same length L, the inclination of the cam grooves 12 is $\theta_1$ for the wide angle of view and $\theta_2$ for the narrow angle of view and ratios of the amounts of rise and fall of the indicating index 19 to the amounts of back and forth movement of the objective lens 9 are different from each other. Hence, a function which is applicable to both of the wide and the narrow angles of view can be given by the same structure.

Figure 17:
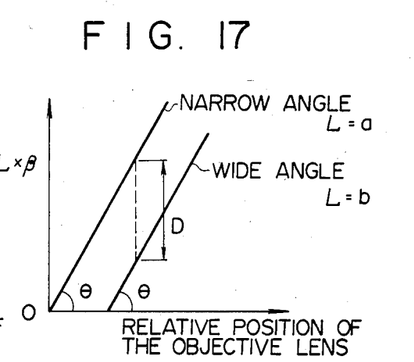
FIG. 17 is a diagram illustrating a relationship of the product of a reference length and a magnification to a relative position of the objective lens in the endoscope shown in FIG. 12.

It is to be noted, however, that when the reference length L is changed to either the wide or the narrow angle of view, the inclinations of the cam groove 12 can be made equal. Specifically, as shown in FIG. 17, assuming that the reference length is a for the narrow angle of view and b for the wide angle of view, when the product of the reference length and a magnification $L \times \beta$ is plotted to a relative position of the image transmitter 5 to the objective lens 9, two parallel straight lines (inclination $\theta$) will be obtained. Ratios of the amounts of up and down movement of the index 19 to the amounts of back and forth movement of the objective lens 9 can be made equal for both of the wide and the narrow angles of view. In addition, a difference D between the two parallel lines in the direction of Y axis is made equal to the distance between stationary reference indexes 43 and 44.

Figure 14A:
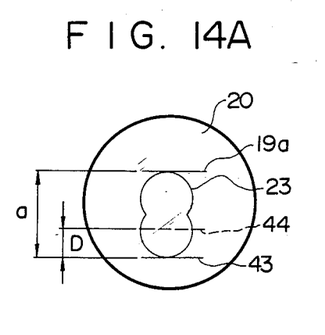
FIGS. 14A and B are explanatory views of respective examples of visual fields viewed from the eyepiece portion shown in FIG. 13.
Figure 14B:
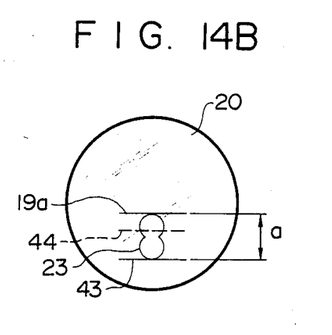
Figure 15A:
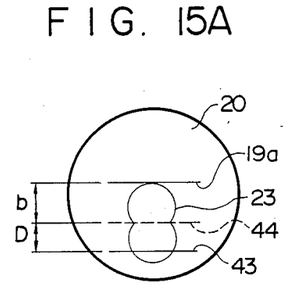
FIGS. 15A and B are explanatory views of respective other examples of visual fields viewed from the eyepiece portion.
Figure 15B:
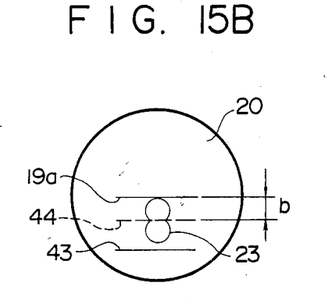

With the structure just described, for the narrow angle of view, as shown in FIGS. 14A and B, the reference length a is always indicated by the stationary reference index 43 for the narrow angle of view in an infocus condition and for the wide angle of view, as shown in FIGS. 15A and B, the reference length b is indicated by the stationary reference index 44 for the wide angle of view.

As described above, when the stationary reference indexes 43, 44 for the narrow and the wide angles of view are disposed on the image exit end plane of the image transmitter 5 at a given distance D as a stationary indication of reference, it is possible to use the structure for respective angles of view without losing the measuring function even when an angle of view is changed.

Figure 18:
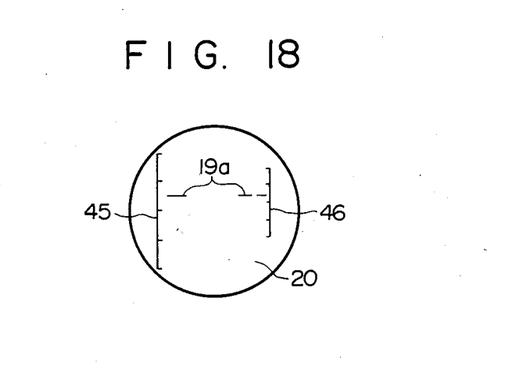
FIG. 18 is an explanatory view of a visual field illustrating modifications of an indicating index and a stationary reference index in the endoscope shown in FIG. 12.

While, in the above mentioned embodiment, the stationary reference indexes 43, 44 which are provided on the glass plate 20 are formed by a horizontally extending line and an object length is measured by indicating the distance between the reference indexes 43, 44 and the image 19a of the indicating index 19, a scale indicating a magnification of the objective optical system 3 or an overall magnification of observation may be provided on the glass plate 20 as first and second stationary reference indexes 45, 46, as shown in FIG. 18. Alternatively, a scale indicating a distance between the objective optical system 3 and an object to be observed may be used as first and second stationary reference indexes. It will be understood that these first and second stationary reference indexes correspond to the narrow and the wide angles of view of the objective optical system.

The present invention is not limited to an endoscope having an image guide of optical fibers flux as an image transmitter but also is applicable to an endoscope having a relay lens system or having a solid state pick-up device such as a charge-coupled-device. In the latter case, the stationary reference index may be displayed on a cathode-ray tube. In addition, it is to be noted that a liquid crystal plate may be used for a member on which the reference index is formed, which plate is selectively controlled by turning ON or OFF a voltage to display the reference index or not.

Furthermore, while in each of the foregoing embodiments, the stationary reference index is formed on the glass plate by means of an evaporation operation, the present invention is not limited to this and the stationary reference index may be formed by directly applying an evaporation operation on an image receiving end plane or an image exit end plane of the image transmitter. By constructing the reference index as described above, a glass plate for the stationary reference index is dispensed with and thus the construction may be simplified. In addition, it is to be noted that a drive mechanism for moving up and down or turning the glass plate for the indicating index in cooperation with back and forth movement of the objective optical system may be a lifting mechanism including a combination of inclined cams, a connecting wire, or the like.

What is claimed is:

1. An endoscope comprising:
   an objective optical system disposed in the distal end portion of said endoscope and having a movable member which is movable in the direction of the optical axis thereof as a focus adjustment operation is made;
   an image transmitter whose image receiving end plane is optically coupled to said objective optical system so as to transmit an image of an object being observed from said image receiving end plane to an image exit end plane of said image transmitter;
   indicating index means disposed between said objective optical system and said image transmitter;
   a transfer mechanism for allowing said indicating index means to move in a plane perpendicular to the optical axis of said objective optical system in cooperation with the movement of said movable member of said objective optical system;
   an observation optical system for observing said image on said image exit end plane of said image transmitter; and
   stationary reference index means disposed between said image transmitter and said observation optical system.

2. An endoscope according to claim 1 in which said transfer mechanism is a cam mechanism.

3. An endoscope according to claim 2 in which said indicating index means includes a horizontal line which is formed on a transparent plate and said cam mechanism includes a cam groove formed on said movable member so as to form an acute angle with said optical axis, a control groove formed on a stationary member in a direction perpendicular to said optical axis and a follower pin projecting from said transparent plate in a direction perpendicular to both said optical axis and said control groove so as to fit into the intersection between said cam groove and said control groove, whereby said indicating index moves in a plane lying perpendicular to said optical axis.

4. An endoscope according to claim 3 in which said stationary reference index means is a horizontal line and is positioned in such a manner that a distance between said indicating index means and said stationary reference index means as viewed from said eyepiece optical system side coincides with an image of a predetermined reference length in the real space which is viewed from said eyepiece optical system, so that an actual size of an object being observed can be measured based on said distance.

5. An endoscope according to claim 3 in which said stationary reference index means is a scale indicating a magnification of said objective optical system so that a magnification of said objective optical system can be read from said scale and said indicating index means.

6. An endoscope according to claim 3 in which said stationary reference index means is a scale indicating a distance to an object being observed so that said distance can be determined as a function of said scale and said indicating means.

7. An endoscope according to claim 4 wherein the angle of view of said endoscope may be changed between first and second values using a view converting apparatus and wherein first and second stationary reference index means are provided, said first and second stationary reference index means being positioned in accordance with said first and second values of angle of view, respectively.

8. An endoscope according to claim 7 in which said angle of view converting apparatus comprises an optical adapter having wherein said angle of view changing lens and an angle of view of said objective optical system is selectively switched by the presence or the absence of said angle of view changing lens in response to the mounting or the non-mounting of said optical adapter on the endoscope.

9. An endoscope according to claim 2 in which said indicating index means is formed on a transparent plate by a radial line extending toward said optical axis and said cam mechanism comprises a cam groove provided on said movable member so as to be inclined with respect to both said optical axis and a plane perpendicular to said optical axis, a control groove provided on a stationary member in the circumferential direction perpendicular to the optical axis and a follower pin projecting from said transparent plate in a direction perpendicular to said optical axis so as to fit in the intersection between said cam groove and said control groove, whereby said indicating index means rotates about said optical axis.

10. An endoscope according to claim 9 in which said stationary reference index means is formed by a circular arc-shaped scale indicating a magnification of said objective optical system so that a magnification of said objective optical system can be read determined from the relative position of said scale and said indicating index means.

11. An endoscope according to any one of claims 1 to 10 in which said stationary reference index means is formed on the inner surface of a transparent plate which is located at the image exit end plane of said image transmitter.

12. An endoscope according to claim 11 in which said stationary reference index means is formed on said transparent plate by means of an evaporation operation.

13. An endoscope according to claim 3 or 9 in which said indicating index means is formed on said transparent plate by means of an evaporation operation.

14. An endoscope according to claim 1 in which said objective optical system comprises a lens barrel and an objective lens disposed within said lens barrel and is movable by operation of an operating wire which is moved during a focus adjustment operation.

15. An endoscope according to claim 1 in which said image transmitter is formed of an optical fiber bundle.

16. An endoscope according to claim 1 in which said observation optical system comprises an eyepiece disposed within an eyepiece portion of the endoscope.

* * * * *